United States Patent [19]
Bayon et al.

[11] Patent Number: 5,654,290
[45] Date of Patent: Aug. 5, 1997

[54] POLYUNSATURATED FATTY ACID BASED DRUGS

[75] Inventors: Yves Bayon, Venissieux; Martine Croset, Bron; Michel Lagarde, Chassieu; Jean Lecerf, Genlis; Frank Thies, Dijon; Jean-Louis Tayot, La-Tour-de-Salvagny; Véronique Chirouze, Sainte-Foy-les-Lyon, all of France

[73] Assignees: Institut National de la Sante et de la Recherche Medicale, Paris; Imedex, Chaponost, both of France

[21] Appl. No.: 256,825

[22] PCT Filed: Nov. 24, 1993

[86] PCT No.: PCT/FR93/01158

§ 371 Date: Sep. 21, 1994

§ 102(e) Date: Sep. 21, 1994

[87] PCT Pub. No.: WO94/12170

PCT Pub. Date: Jun. 9, 1994

[30] Foreign Application Priority Data

Nov. 24, 1992 [FR] France ................................. 92 14078

[51] Int. Cl.$^6$ .................................................. A61K 31/685
[52] U.S. Cl. ........................... 514/77; 514/76; 514/78
[58] Field of Search ............................. 514/76, 77, 78

[56] References Cited

U.S. PATENT DOCUMENTS 5,135,921  8/1992  Della Valle et al. ...................... 514/77

*Primary Examiner*—Brian M. Burn
*Attorney, Agent, or Firm*—Larson & Taylor

[57] ABSTRACT

Drug compositions comprised of therapeutically effective amounts of at least one compound selected from the group consisting of:

DHA esterified in the form of lysophosphatidyl-choline (lyso-PCDHA) in position sn-2;

DHA-phosphatidylcholines (PCDHAs) in which DHA is esterified in position sn-2 and which have an acyl group of [very short length] 2 to 6 carbon atoms in position sn-1;

and triglycerides in which DHA is esterified in position sn-2 and which have acyl groups of [very short length] 2 to 6 carbon atoms in positions sn-1 and sn-3.

9 Claims, 3 Drawing Sheets

POLYUNSATURATED FATTY ACID BASED DRUGS

This is a 371 of PCT/FR93/01158, filed Nov. 24, 1993.

The present invention relates to new drugs based on polyunsaturated fatty acids, and more precisely based on docosahexaenoic acid (also called DHA or 22:6n-3).

It is known that nervous tissues are very rich in essential polyunsaturated fatty acids (1, 2), especially in DHA which can represent 24% of the fatty acids of the phosphatidylethanolamines (PE) of the grey matter (3). Polyunsaturated fatty acids play an important role in normal cerebral development (4). Thus, dietary deficiency of essential unsaturated fatty acids or the disruption of their metabolism during a period of cerebral development might affect myelinization in man (1, 5). As regards more particularly the fatty acids of the n-3 family, it has been shown that a dietary deficiency of these fatty acids results in a faulty pre- and post-natal development of the retina and of the brain in Rhesus monkeys (6, 7) and other animals (8). It seems, in addition, that these fatty acids are involved in the capacity for learning in young rats (9, 10). The brain does not accumulate 18:3n-3, the precursor of 22:6n-3 or DHA, on the one hand because it has the enzymes for elongation and unsaturation necessary for the conversion of 18:3n-3 into 22:6n-3 (11) and, on the other hand, because it can capture the 22:6n-3 attached to the plasma albumin produced by the liver (12, 13) because the brain captures non-esterified fatty acids better if they are unsaturated (14, 15).

On the basis of the oldest of these studies, it has already been proposed to provide the body with essential polyunsaturated fatty acids, in the form of nutrients or preparations which can be administered by other routes. In particular, several documents have insisted on the value of providing, in this manner, essential polyunsaturated acids such as 18:3n-3, arachidonic acid and 22:6n-3. In the preparations envisaged, these fatty acids are present in various forms, in general mixed and especially in the form of triglycerides, phospholipids and also in non-esterified form. Some of these documents underline the value of administering these essential fatty acids in the form of components of phospholipids.

It has, moreover, been shown that diets rich in eicosapentanoic acid (20:5n-3) and in the acid 22:6n-3 decrease the incidence of cardiovascular diseases (16). The mechanisms responsible for the beneficial effects of these fatty acids remain, however, to be specified. Numerous studies have focussed on the effects of these polyunsaturated fatty acids on platelet functions. It has been shown that these fatty acids, like other cis-unsaturated fatty acids, inhibit platelet aggregation induced by a wide variety of platelet activators including U 46.619, an agonist of the receptor for thromboxane ($TXA_2$) and prostaglandin $H_2$ ($PGH_2$) (17–23). The inhibitory effects of 20:5n-3 and 22:6n-3 would be exerted at several levels (17–19, 24–27). Moreover, it has been shown that non-esterified 20:5n-3 and 22:6n-3 competitively inhibit platelet aggregation induced by U 46.619 as well as the specific binding of the latter to washed platelets (28). The incorporation in vitro of 20:5n-3 and of 22:6n-3 into the platelet lipid reserves, by means of albumin, also results in the loss of aggregability of the platelets in response to U 46.619 and a decrease in the affinity of the agonist for its receptor (29). In this study, if 20:5n-3 and 22:6n-3 have been predominantly esterified in the phospholipids, the effects observed can also be attributed to the enrichment of the other lipid fractions in these fatty acids. 20:5n-3 and 22:6n-3 exhibit a certain selectivity of action on the $TXA_2/PGH_2$ receptor since none of these fatty acids affects the platelet aggregation induced by thrombin and by the ionophore A 23187, when used at concentrations which do not bring this receptor into play (29). Furthermore, they do not modify binding of yohimbine to the $alpha_2$-adrenergic receptor of the platelet membranes (30), which exhibits a certain structural homology. Among all the fatty acids tested, only 20:5n-3 and 22:6n-3 specifically alter the $TXA_2/PGH_2$ receptor of whole platelets (29) or of solubilized platelet membranes (30). 22:6n-3 appears to be more effective than 20:5n-3.

The use of "natural" phosphatidylcholines obtained from fish containing docosahexaenoic acid in position sn-2 (PCDHAn) as anticholesterolemics, anti-thrombotics and platelet aggregation inhibitors has been described in application JP-A-64 50890 by Nishizawa et al. (31).

The use of PCDHAn as antitumour agents has been described in application JP-A-1,160,989 by Hibino et al. (32).

Moreover, the use of DHA-lysophosphatidylcholine in position sn-1 as antitumour agent has been described by Sakurai et al., in application JP-A-1,203,330 (33).

The present invention is intended to provide new essential polyunsaturated fatty acid-based drugs exhibiting a very high efficacy. One of the objectives is thus to produce a new drug with anti-thromboxane $A_2$ effect which is extremely effective.

Another objective of the invention is to produce a new drug which makes it possible to take into the brain an essential fatty acid with a particularly high efficacy.

The invention has made it possible to discover, surprisingly, that the efficacy, in the abovementioned applications, of 22:6n-3 or DHA should be attributed to its esterification in phosphatidylcholines (PC), excluding other forms of phospholipids and especially phosphatidylethanolamines (PE), and this both in the application as anti-thromboxane $A_2$, and as source of essential polyunsaturated fatty acid supplied to the brain. Furthermore, the efficacy of DHA in this form is particularly high compared with the efficacy of other essential fatty acids such as linoleic acid (18:2n-6), including in the form of phosphatidylcholine (PC).

The administration per os of natural phosphatidylcholines containing long-chain fatty acids is however faced with the slowness of their digestion. Now, in numerous cases, intravenous administration is not desirable.

The invention therefore has an important aim, that of providing drugs which meet the abovementioned objectives, which can be administered very effectively, orally, and which, furthermore, are distributed with an increased efficacy, to the recipient cells.

The subject of the invention is new essential fatty acid-based drugs, characterized in that they comprise, in a therapeutically effective quantity, at least one compound chosen from the group consisting of:

DHA esterified in the form of lysophosphatidylcholine (lyso-PCDHA) in position sn-2;

DHA-phosphatidylcholines in which DHA is esterified in position sn-2 and which have an acyl group of very short length in position sn-1; these compounds are called here PCDHAs;

and triglycerides in which DHA is esterified in position sn-2 and which have acyl groups of very short length in positions sn-1 and sn-3.

Acyl group of very short length is understood to mean an acyl group which may comprise 2 to 6 carbon atoms, mainly acetyl, and optionally propionyl and butyryl.

The compounds used in the drugs according to the invention are acylated in position sn-1 (and sn-3 in the case of triglycerides) by synthesis.

Preferably, the drugs comprise, at least 70% DHA in the class of fatty acids esterified in position sn-2 of phosphatidylcholines, or triglycerides in a therapeutically effective quantity, and preferably more than 10%.

In a preferred embodiment, the medicinal composition may be pure, that is to say contain only the abovementioned compound(s) as source of polyunsaturated essential fatty acid.

In an advantageous embodiment for the intracerebral binding, the drug contains, as active ingredient, DHA esterified in the form of lysophosphatidylcholine (lyso-PCDHA) with, preferably, at least 70% DHA in the class of polyunsaturated essential fatty acids esterified in position sn-2 of lyso-PCDHA, and particularly greater than 10%.

Each dose of drug according to the invention comprises a therapeutically effective quantity of PDCHAs or lyso-PCDHA.

The subject of the invention is also the use of the abovementioned compounds for the preparation of a drug with platelet aggregation-inhibiting effect, which can be used especially for the preventive or curative treatment of cardiovascular diseases, including atheromatous disease.

The subject of the invention is also the use of the abovementioned compounds for the preparation of a drug intended for the treatment of cerebral essential fatty acid insufficiencies or deficiencies, especially in the premature, infants, those suffering from denutrition and the elderly.

The drugs according to the invention can be prepared for oral or parenteral and especially intravenous administration, or by the rectal route or by any other route of administration and especially in the form of collyrium for ophthalmic use.

The preparations for oral administration may contain any customary excipient or vehicle, for example those already used for the administration of essential fatty acids. They may consist of powders, granules, solutions and the like, and may optionally incorporate other active ingredients.

For parenteral administration, the drug is preferably produced in the form of a perfusion solution having the usual composition of these solutions and in which the concentration of PCDHAs (preferably in the form of liposomes or linked to albumin) or of lyso-PCDHA (linked to albumin) or of triglycerides-DHA is preferably of the order of 1 to 100 mg/liter of either of the lipid forms of DHA.

The oral administration may be isolated, via a cure of several days or several weeks or chronic. The dosage is preferably of the order of 1 to 100 mg per kg per day.

The PCDHAs and the lyso-PCDHA can be obtained by chemical synthesis and/or by biosynthesis, especially from starting products (fatty acids, phospholipids, triglycerides) extracted and purified from the usual sources such as placenta, algae, eggs, fish, animal organs and plants such as soya bean.

The PCDHAs can pass more easily across the intestinal barrier without being degraded. If they are hydrolysed by lipase activities acting both in position sn-1 and in position sn-2, the acetic, propionic, butyric and caproic acids will be preferably hydrolysed compared with the long-chain fatty acids in position sn-2 and, more particularly, compared with DHA, which is known to be difficult to hydrolyse with human lipases. For example, if the PCDHAs are hydrolysed by pancreatic lipase, they will cross the intestinal barrier exclusively or practically in the form of 1-lyso-2-DHA-glycerophosphocholine (designated hereinafter lyso-PCDHA) whose reesterification into PCDHAn is favoured in the enterocytes. The PCDHAs can also be easily hydrolysed by lipases specific for position sn-1. The result is that a zero or small proportion of the DHA of the PCDHAs will be in non-esterified form after the administration of the PCDHAs. Consequently, since the conversion of DHA into eicosapentaenoic acid (EPA) is known to occur with the non-esterified fatty acid, it can be totally or practically suppressed in vivo. The formation of EPA from the administered PCDHA's should be avoided because EPA has activities which are distinct from DHA (Yon Schacky et Weber, 1985 (34); Triggiani et coll., 1990 (35); Robinson, 1993 (36); Salem et Ward, 1993 (37)) and contributes towards reducing the activity of DHA in some cases (Carlson et coll., 1992 (38); Carlson, 1993 (39)).

After administration of the PCDHAs (intravenous or per os), a significant proportion of the PCDHAs is converted to lyso-PCDHA which can be reacylated with long-chain fatty acids to give PC's which are equivalent to the PCDHAn's or combine with carriers such as albumin. By being intact, the PCDHAs compared with PCDHAn's also have the advantage of binding better to albumin in vitro or of being transported better in vivo by albumin. Compared with the PCDHAn's, the PCDHAs can thus have a fate closer to that of lyso-PCDHA which has been described below as a favoured form of supply of DHA to the brain. Albumin is also known to efficiently transport fatty acids or in the form of lysophospholipids to the cells, especially the platelets.

On the other hand, the PCDHAs like the PCDHAn's can combine with various lipoproteins such as the HDL's. Consequently, it also has a metabolism close to that of the PCDHAn's. They can thus reduce the plasma concentration of pro-atherogenic cholesterol combined with the LDL's, by facilitating the transfer of cholesterol from the LDL's to the HDL's as observed with PC's containing long-chain fatty acids of which at least one is polyunsaturated (Kirsten et coll., 1989 (40); O'Brien et coll., 1993 (41)). This property of the PCDHAs can thus contribute to decreasing the incidence of cardiovascular diseases.

The PCDHAs therefore have novel properties compared with the PCDHAn's prepared from fish (Hibino et al (32); Nishizawa et al. (31)) and which are known not to have in position sn-1 short-chain fatty acids (fatty acids comprising up to 6 carbon atoms) (Sargent et al., 1990 (42)). In addition to their own activities, they can behave both like lyso-PCDHA's and PCDHAn's. In particular, like the PCDHAn's, they have the advantage of being administerable in the form of liposomes, in principle, via all the routes available including the intravenous route, which is known to facilitate the supply of drugs to the brain. To a certain extent, they also constitute a stable galenic form of the lyso-PCDHA's. Indeed, the PCDHAs are partially hydrolysed to lyso-PCDHA in vivo. Moreover, the acylation of the position sn-1 of the lyso-PCDHA's avoids the formation of 1-DHA-2-lyso-glycerophosphocholine during the storage of the lyso-PCDHA's before their administration, or even after their administration. 1-DHA-2-lyso-glycerophosphocholine is a phospholipid whose use as antitumour agent has been described (Sakurai et al. (33)). Its formation should be avoided because this compound has a metabolism which is potentially different from the lyso-PCDHA's (Morash et coll., 1989 (43)).

Other advantages and characteristics of the invention will appear on reading the following description, prepared by way of non-limiting example and with reference to the accompanying drawing in which:

The diacyl-glycerophosphocholines of the platelet membranes were replaced either with 1-palmitoyl-2-docosahexaenoyl-glycerophosphocholine (bars with vertical stripes, "22:6n-3"), or with 1-palmitoyl-2-linoloyl-glycerophosphocholine (bars with horizontal stripes, "18:2n-6"), using the endogenous transfer protein of the platelets which is specific for the phosphatidylinositols and phosphatidylcholines. The control platelet membranes (black bars, "control") are obtained by incubation without addition of phospholipids. The data for the graph represent the mean±S.D. of three independent tests.

Figure 1:
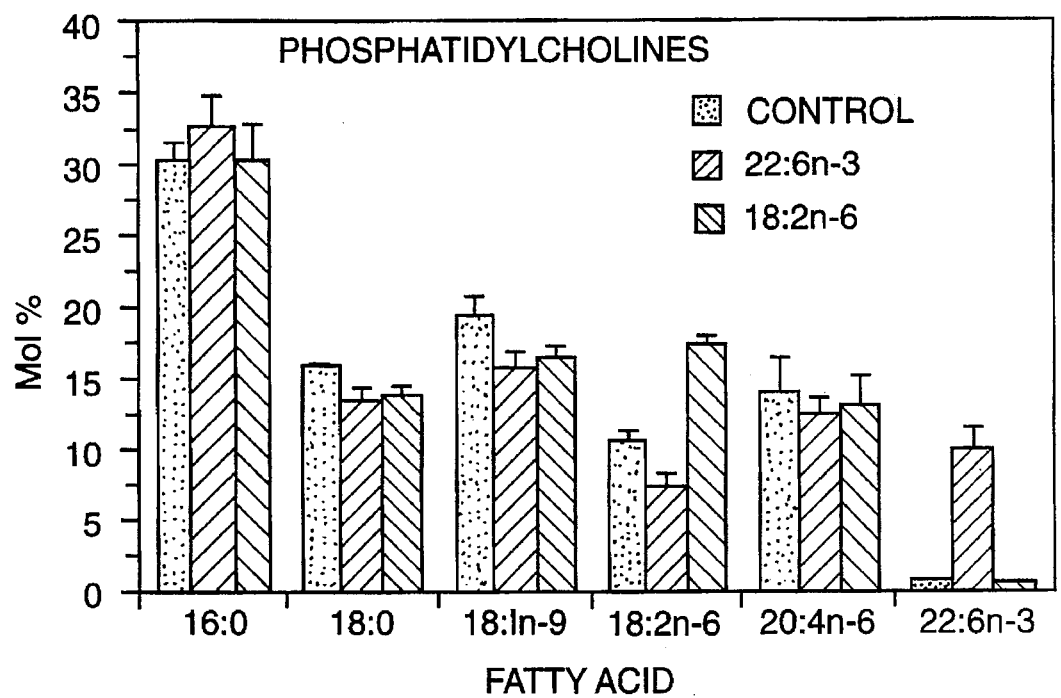
FIG. 1 represents the fatty acid composition of the diacyl-glycerophosphocholines of the platelet membranes after transferring 1-palmitoyl-2-docosahexaenoylglycerophosphocholine (PC-22:6) and 1-palmitoyl-2-linoloyl-glycerophosphocholine (PC-18:2).
Figure 2:
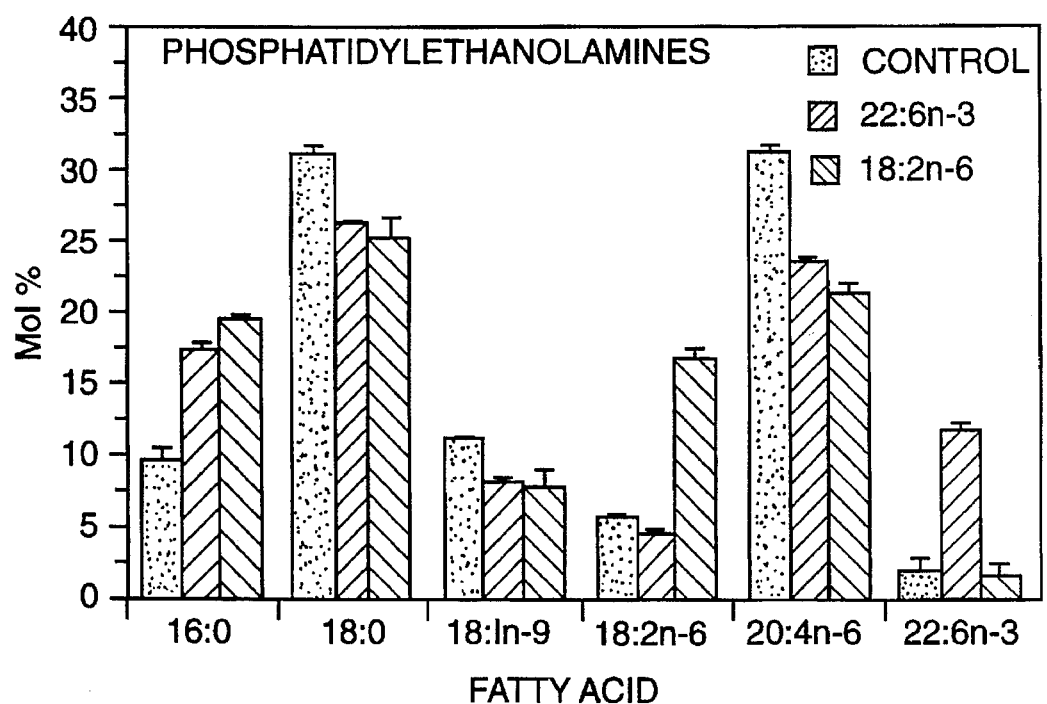
Figure 3A:
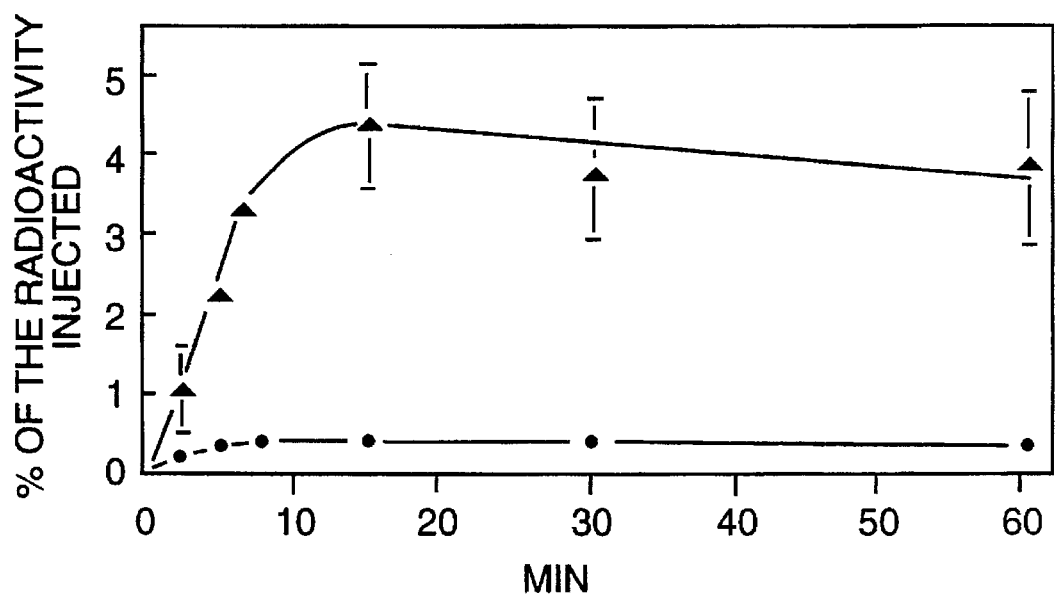
Figure 3B:
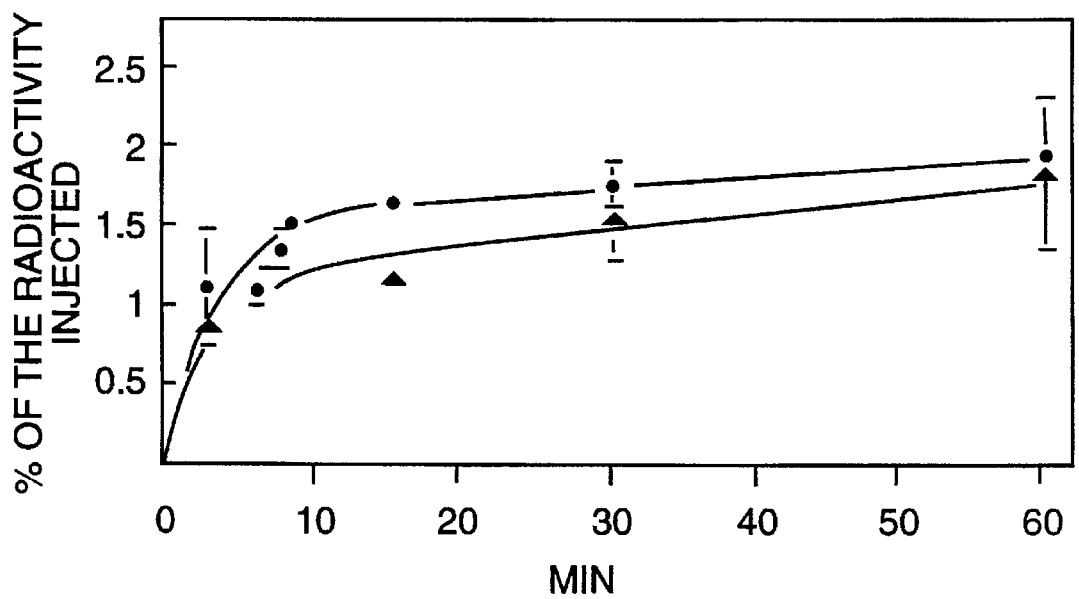
Figure 3C:
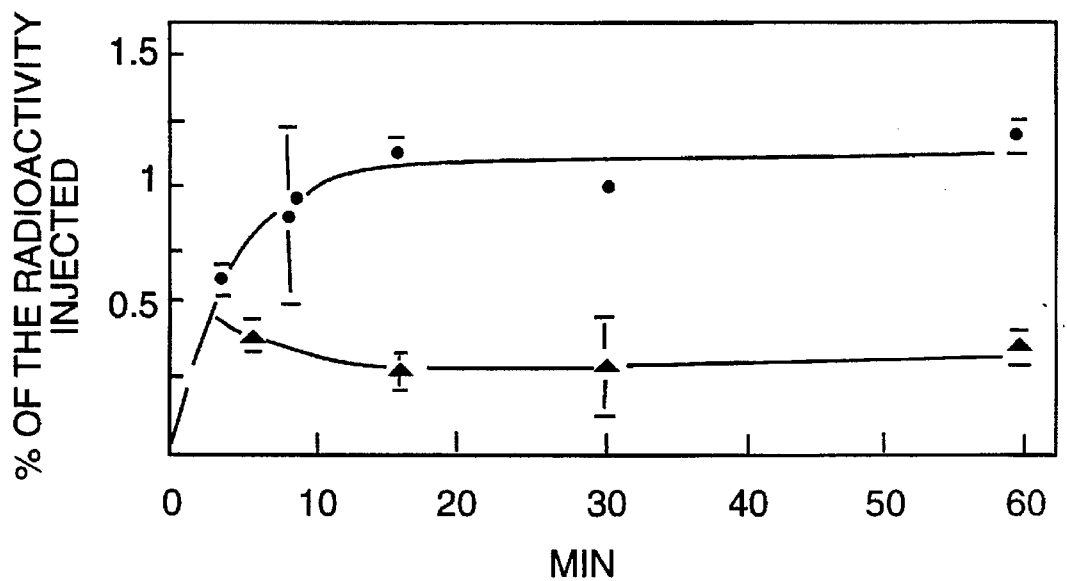
Figure 3D:
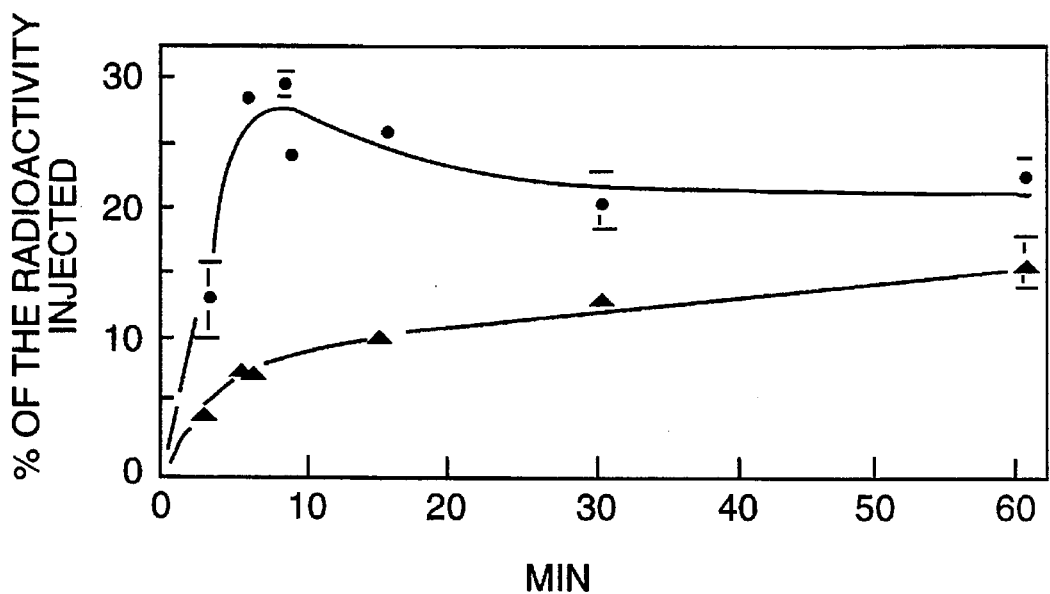

FIG. 2 represents the fatty acid composition of the diacyl-glycerophosphoethanolamines of the platelet membranes after transferring 1-palmitoyl-2-docosahexaenoyl-glycerophosphoethanolamine (PE-22:6 and 1-palmitoyl-2-linoloyl-glycerophosphoethanolamine (PE-18:2).

The diacyl-glycerophosphoethanolamines of the platelet membranes were replaced either with 1-palmitoyl-2-docosahexaenoyl-glycerophosphoethanolamine (bars with vertical stripes, "22:6n-3"), or with 1-palmitoyl-2-linoloyl-glycerophosphoethanolamine (bars with horizontal stripes "18:2n-6"), using the lipid transfer protein purified from maize. The control platelet membranes (black bars, "control") are obtained by incubation without addition of phospholipids. The data for the graph represent the mean±S.D. of three independent tests.

FIG. 3 represents the variation of the radio-activity recovered in the total lipids: A from the brain, B from the kidney, C from the heart and D from the liver, after injecting tritiated DHA in free form (black circle) or in the form of 2-DHA-1-lyso-PC (black triangle).

EXAMPLE 1

Preparation of a composition purified in relation to lyso-PCDHA and PCDHAs from phosphatidylcholines (PC) from algae.

a) Culture of microalgae producing PCDHA

A heterotrophic dinoflagellate, Crypthecodinium cohnii, is cultured in AXM medium at 25° C. The cultures are aerated and stirred under the conditions described by BEACH and HOLZ (44). After culturing for 4 days, the cells are recovered by centrifugation and the moist biomass is freeze-dried. A fermenter containing 10 liters of medium makes it possible to obtain under these conditions about 3 g of freeze-dried biomass.

b) Extraction of the lipids

In a first stage, the neutral lipids are extracted from the freeze-dried biomass with hexane according to the procedure conventionally used for vegetable oils.

In a second stage, the biomass is taken up in an alcoholic solvent (methanol or ethanol) for the extraction of the polar lipids and in particular the phospholipids according to the procedure described in European Patent No. 0,298,787.

This process makes it possible to extract about 18% of neutral lipids and 12% of polar lipids (contents expressed in weight and expressed in terms of the freeze-dried biomass).

c) Purification of the phosphatidylcholines containing DHA in position sn-2.

The phosphatidylcholine containing DHA is isolated from the polar lipids by high-performance liquid chromatography (HPLC) according to the procedure described by CHRISTIE et al. (45). The treatment of the entire polar lipids obtained from 10 liters of culture (about 360 mg) makes it possible to purify about 180 mg of PCDHA. The phosphatidylcholine obtained contains 66% DHA (content expressed in weight of total fatty acids esterified on the PC).

d) Preparation of the lyso-PCDHA's.

The acyl chains in position sn-1 of the phosphatidylcholines purified as indicated above are hydrolysed by any lipase having a phospholipase $A_1$ activity. The lyso-PCDHA obtained is purified by chromatography.

e) Preparation of the PCDHAs.

The lyso-PCDHA described above can be reacylated by organic synthesis to obtain the PC-DHA's acylated with the acetic, propionic, burytic or caproic acids in position sn-1 (Delfino et coll., 1987 (46)). The PCDHAs obtained are then purified by chromatography.

EXAMPLE 2

Preparation of a composition purified in relation to PC-DHAs by semisynthesis from glycerophosphorylcholine or glycerophosphate.

a) Diacylation of the glycerophosphocholine and the glycerophosphate with acetic, propionic, butyric, caproic or docosahexaenoic acids.

The glycerophosphate is acylated with derivatives of acetic, propionic, burytic, caproic or docosahexaenoic acids (acyl anhydride, acyl chloride, acyl imidazolide and the like) to give a diacylphosphatidic acid (PA). The PA formed is then converted to PC using choline chloride (Schena et Davis, 1989 (47); Walts et coll., 1992 (48)).

The PC's can be obtained more directly by acylating the glycerophosphorylcholine with the derivatives of acetic, propionic, butyric, caproic or docosahexaenoic acids as described above.

b) Preparation of the PCDHAs from PC's containing the acetic, propionic, burytic or caproic residues in position sn-1 and sn-2.

The PC's containing the acetic, propionic, butyric or caproic residues are selectively hydrolysed in position sn-2 by any lipase having a phospholipase $A_2$ activity. The lyso-PC's formed are reacylated with derivatives of DHA (acyl anhydride, acyl chloride, acyl imidazolide and the like) to give PCDHAs.

c) Preparation of the PCDHAs from PC's containing the docosahexaenoic residue in position sn-1 and sn-2.

The PC containing the DHA residue is selectively hydrolysed in position sn-1 by any lipase having a phospholipase $A_1$ activity. The lyso-PC's formed are reacylated with derivatives of acetic, propionic, butyric or caproic acids (preferably acyl anhydride or acyl chloride) to give PCDHAs.

EXAMPLE 3

Study of the anti-thromboxane $A_2$ effect of the 1-acyl-2-docosahexaenoyl-glycerophosphocholines.

Preparations of esterified DHA into various classes of phospholipids were carried out using phospholipid transfer proteins in order to enrich, in a specific manner, the phosphatidylcholines (PC) and the phosphatidylethanolamines (PE) of the platelet membranes in linoleic acid (18:2n-6) and in DHA (49). In particular, the transfer protein (PT), which is specific for the PC's and purified from bovine liver, was used to modify the composition of molecular species of the PC's of erythrocytes (49).

In the procedure used in the present example, the endogenous quantity of platelet phospholipids is not altered by the transfer carried out by means of the maize or platelet PT; nevertheless, the phospholipids were enriched in 18:2n-6 or in DHA.

The influence of the fatty acids on the $TXA_2/PGH_2$ receptor was established by measuring the specific binding of tritiated SQ29,548, a competitive antagonist of the $TXA_2/PGH_2$ receptor, to platelet membranes whose PC's or PE's are enriched either in 18:2n-6 or in DHA.

Only the platelet membranes containing PC's enriched in DHA alter the $TXA_2/PGH_2$ receptor by significantly increasing the dissociation constant of SQ29.548. The enrichment of the PC's of the platelet membranes in 18:2n-6 and of the PE's in 18:2n-6 or in DHA has no effect on the receptor (Table I).

These properties cause the PCDHAs to be considered, at a therapeutically active concentration, as a drug having an aggregation-inhibiting and an anti-hypertensive activity by its anti-thromboxane $A_2$ effect.

TABLE $I_A$

Binding of SQ 29.548 to the $TXA_2/PGH_2$ receptor of the platelet membranes containing PC's enriched in DHA (22:6n-3) and in 18:2n-6.

|  | $K_d$ (nM) | $B_{max}$ (pmol/mg prot.) | Hill Coefficient |
|---|---|---|---|
| Control | 4.17 | 2.57 | 0.82 |
|  | 6.10 | 1.84 | 1.01 |
|  | 3.24 | 2.03 | 0.94 |
|  | 4.50 ± 1.46 | 2.15 ± 0.38 | 0.92 ± 0.10 |
| PC 22:6n-3 | 5.69 | 2.94 | 0.91 |
|  | 8.56 | 2.09 | 1.00 |
|  | 7.05 | 2.40 | 0.94 |
|  | 7.10 ± 1.44 (a) | 2.48 ± 0.43 | 0.95 ± 0.05 |
| PC 18:2n-6 | 4.05 | 2.41 | 0.90 |
|  | 4.64 | 1.83 | 1.00 |
|  | 3.16 | 1.91 | 0.94 |
|  | 3.95 ± 0.75 | 2.05 ± 0.31 | 0.95 ± 0.05 |

(a) p < 0.05 compared with the control and with PC 18:2n-6

TABLE $I_B$

Binding of SQ 29.548 to the $TXA_2/PGH_2$ receptor of the platelet membranes containing PE's enriched in DHA (22:6n-3) and in 18:2n-6.

|  | $K_d$ (nM) | $B_{max}$ (pmol/mg prot.) | Hill Coefficient |
|---|---|---|---|
| Control | 3.36 | 1.86 |  |
| 0.93 | 4.43 | 2.37 | 1.05 |
|  | 4.63 | 1.17 | 1.04 |
|  | 4.14 ± 0.68 | 2.13 ± 0.26 | 1.01 ± 0.07 |
| PE 22:6n-3 | 2.92 | 1.67 | 0.95 |
|  | 4.61 | 1.99 | 1.02 |
|  | 4.63 | 1.91 | 1.02 |
|  | 4.05 ± 0.98 | 1.86 ± 0.17 | 1.00 ± 0.04 |
| PE 18:2n-6 | 3.11 | 1.89 | 0.94 |
|  | 4.31 | 2.26 | 1.00 |
|  | 4.92 | 2.07 | 1.05 |
|  | 4.11 ± 0.92 | 2.07 ± 0.19 | 1.00 ± 0.06 |

EXAMPLE 4

Study of the capture by the brain, in rats, of the 2-acyl, 1-lysophosphatidylcholines (lyso-PC).

The animal studied is a 20-day-old rat in which the cerebral lipid metabolism is at its peak.

The lyso-PC's are labelled on the fatty acid and the choline, attached to albumin and administered intravenously (50). The results show that, for DHA(22:6n-3), the lyso-PC's containing it are particularly well captured by the brain which is better than the lyso-PC's comprising other fatty acids such as 18:1, 18:2 and 20:4. Only the brain shows such a preference as seen in FIG. 3, since with the exception of the kidney, which captures the two forms of supply in essentially the same manner, namely lyso-PCDHA and DHA in non-esterified form, the liver and the heart do not capture the lyso-PCDHA's as effectively as the non-esterified DHA. It appears that the reacylation of DHA in the phosphatidylcholines is low and is visible only in the first stages after the injection (Table II) because, very rapidly, a differential esterification is produced in the phosphatidylethanolamines. It therefore appears that the lyso-PCDHA's attached to albumin constitute a particularly preferred form of supply of DHA to the developing brain.

TABLE II

Distribution of the radioactivity between the lipid classes of the brain (in % of the radioactivity of the total lipids)

A. Injections of Lyso-PCDHA

|  | 2.5 min | 5 min | 6.5 min | 15 min | 30 min | 60 min |
|---|---|---|---|---|---|---|
| Lyso-PC | 4.1 | 0.4 | 1.2 | 0.2 | 0 | 0 |
| PI | 8.9 | 3.4 | 3.7 | 3.2 | 2.6 | 2.6 |
| PS | 3.9 | 5.3 | 5.3 | 4.6 | 5.0 | 3.9 |
| PC | 25.6 | 17.8 | 26.2 | 26.8 | 24.1 | 24.9 |
| PE | 28.2 | 26.3 | 28.1 | 38.9 | 46.4 | 49.2 |
| OTHERS | 0 | 11.4 | 3.7 | 2.6 | 3.8 | 5.3 |
| LN | 29.3 | 35.3 | 31.6 | 23.7 | 17.8 | 16.7 |
| MG | 2.2 | 2.3 | 2.7 | 1.8 | 0.7 | 0.4 |
| DG | 10.8 | 9.3 | 9.4 | 5.8 | 4 | 2.6 |
| AG | 15.3 | 21.2 | 17.2 | 13.9 | 11 | 10.0 |
| TG | 1.0 | 2.5 | 2.3 | 2.3 | 2.1 | 1.4 |

B. Injections of non-esterified DHA

|  | 2.5 min | 5 min | 7.5 min | 8 min | 15 min | 30 min | 60 min |
|---|---|---|---|---|---|---|---|
| PI | 2.7 | 5.1 | 2.6 | 3.8 | 3 | 3.4 | 2.8 |
| PC | 18.8 | 23.2 | 21.1 | 19.6 | 25.7 | 24.8 | 24.3 |
| PS | 4.0 | 4.6 | 1.8 | 4.3 | 2.9 | 2.9 | 6.3 |
| PE | 37.5 | 48.1 | 44.4 | 40.7 | 49.1 | 48.4 | 54.1 |
| LN + AG | 36.7 | 19.0 | 30.0 | 31.6 | 20.8 | 20.4 | 12.5 |

We claim:

1. A drug composition comprising a therapeutically effective amount of at least one compound selected from the group consisting of:

DHA esterified in the form of lysophosphatidyl-choline (lyso-PCDHA) in position sn-2;

DHA-phosphatidylcholines (PCDHAs) in which DHA is esterified in position sn-2 and which have an acyl group of 2 to 6 carbon atoms in position sn-1;

and triglycerides in which DHA is esterified in position sn-2 and which have acyl groups of 2 to 6 carbon atoms in positions sn-1 and sn-3.

2. Drugs according to claim 1, characterized in that the acyl group is acetyl, propanoyl or butyryl.

3. Drugs according to either of claim 1, characterized in that they comprise at least 70% docosahexaenoic acid (DHA) esterified in position sn-2.

4. Drugs according to claim 1, characterized in that they comprise, as active ingredient, at least 10% docosahexaenoic acid (DHA) esterified in position sn-2 of the lyso-phosphatidylcholines.

5. Drugs according to claim 1, packaged for oral administration.

6. Process for preparing a composition enriched or purified in relation to PCDHAs or to lyso-PCDHA, in which the phospholipids are extracted from a biomass with an alcoholic solvent, and the phosphatidylcholine containing DHA is isolated by high-performance liquid chromatography, then the DHA is hydrolysed by any lipase having a phospholipase $A_1$ activity, the lyso-PCDHA obtained being purified by chromatography.

7. Process according to claim 6, characterized in that the position sn-1 is reacylated by an acid chosen from the group consisting of acetic, propionic, butyric and caproic acid.

8. Process for preparing a composition enriched or purified in relation to PCDHAs, characterized in that a diacylation of the glycerophosphocholine or glycerophosphate is carried out by means of acetic, propionic, burytic or caproic acid or their derivatives, and in that the sn-2 positions are selectively hydrolysed by a phospholipase $A_2$, after which the lyso-PC's formed are reacylated with a DHA derivative.

9. Process for preparing a composition enriched or purified in relation to PCDHAs, characterized in that a diacylation of the glycerophosphocholine or glycerophosphate is carried out by means of DHA acid, and in that the sn-1 positions are selectively hydrolysed by a phospholipase $A_1$, after which the lyso-PCDHA's formed are reacylated by means of acetic, propionic, burytic or caproic acid or one of their derivatives.

\* \* \* \* \*